(12) United States Patent
Jankowski et al.

(10) Patent No.: US 9,417,227 B2
(45) Date of Patent: Aug. 16, 2016

(54) METHODS FOR DETECTING SULFUR

(71) Applicant: United States Gypsum Company, Chicago, IL (US)

(72) Inventors: Michael F. Jankowski, Mundelein, IL (US); Renee J. Weinberger, Waukegan, IL (US)

(73) Assignee: UNITED STATES GYPSUM COMPANY, Chicago, IL (US)

( * ) Notice: Subject to any disclaimer, the term of this patent is extended or adjusted under 35 U.S.C. 154(b) by 0 days.

(21) Appl. No.: 14/518,438

(22) Filed: Oct. 20, 2014

(65) Prior Publication Data

US 2015/0177217 A1 Jun. 25, 2015

Related U.S. Application Data

(60) Provisional application No. 61/919,104, filed on Dec. 20, 2013.

(51) Int. Cl.
  *G01N 33/24* (2006.01)
  *G01N 33/22* (2006.01)
  *G01N 31/22* (2006.01)
  *G01N 21/78* (2006.01)

(52) U.S. Cl.
  CPC ............... *G01N 33/24* (2013.01); *G01N 21/78* (2013.01); *G01N 31/22* (2013.01); *Y10T 436/188* (2015.01)

(58) Field of Classification Search
  CPC ....... G01N 33/24; G01N 33/00; G01N 31/22; G01N 31/00; G01N 21/77; G01N 21/75; G01N 21/00; Y10T 436/18; Y10T 436/00
  USPC .............................. 436/123, 119; 422/430, 50
  See application file for complete search history.

(56) References Cited

U.S. PATENT DOCUMENTS

| | | | |
|---|---|---|---|
| 3,847,552 A | 11/1974 | Hobgood et al. | |
| 4,348,358 A | 9/1982 | McKee et al. | |
| 4,696,906 A | 9/1987 | Funahashi et al. | |
| 5,292,665 A | 3/1994 | Hochstrasser et al. | |
| 5,550,061 A | 8/1996 | Stone | |
| 5,858,307 A | 1/1999 | Neihof | |
| 5,935,862 A | 8/1999 | Novak | |
| 2001/0014304 A1 | 8/2001 | Satokawa et al. | |
| 2008/0081374 A1 | 4/2008 | Takatsu et al. | |
| 2008/0283446 A1 | 11/2008 | Tatarchuk et al. | |
| 2009/0311144 A1 | 12/2009 | Kim et al. | |
| 2010/0278687 A1 | 11/2010 | Mason | |
| 2011/0104684 A1 | 5/2011 | Hooper | |
| 2013/0149788 A1 | 6/2013 | Sacks et al. | |

FOREIGN PATENT DOCUMENTS

| | | |
|---|---|---|
| CN | 101706472 | 5/2010 |
| WO | WO 97/05482 | 2/1997 |
| WO | WO 2013/029106 A1 | 3/2013 |

OTHER PUBLICATIONS

ASTM International, Standard Test Methods for Chemical Analysis of Gypsum and Gypsum Products (Metric), ASTM International, C471M-01, 2006, pp. 1-13.*
ASTM International, Standard Test Method for Chemical Analysis of Gypsum and Gypsum Product, ASTM International, 2006, pp. 1-12.*
Kwasniewski, Misha T. et al., "Convenient, inexpensive quantification of elemental sulfur by simultaneous in situ reduction . . . ", Analytica Chimica Acta, pp. 52-57, 2011.
Search Report from International Patent Application No. PCT/US2014/070849, dated Feb. 27, 2015.

* cited by examiner

*Primary Examiner* — Christine T Mui
(74) *Attorney, Agent, or Firm* — Greer, Burns & Crain, Ltd.; Pradip Sahu; Philip T. Petti (57) ABSTRACT

A method for rapid detection of sulfur in a gypsum sample by causing emission of sulfur from the sample as vapors, reacting the vapors with silver nitrate and detecting sulfur by monitoring for color change. A kit for rapid detection of sulfur in a gypsum sample is also provided. Further methods include those in which the amount of sulfur in a gypsum sample is quantified in colorimetric analysis with silver nitrate and gypsum standards with known concentrations of sulfur.

11 Claims, 9 Drawing Sheets

METHODS FOR DETECTING SULFUR

CROSS-REFERENCE TO RELATED APPLICATIONS

This application claims its priority to U.S. Provisional Application 61/919,104 filed on Dec. 20, 2013, the entire disclosure of which is incorporated herein in its entirety by reference.

BACKGROUND

Various gypsum products including, but not limited to, wall panels, wallboard, partitions, ceiling, flooring, joint compounds, cementitious compositions and fire-resistant coatings, are popular consumer products which are broadly used in building construction and for other applications.

Commonly, raw gypsum, also known as calcium sulfate dihydrate, terra alba or landplaster, is mined from open and underground mines. When gypsum is mined, the natural rock is found in the dihydrate form, having about two water molecules associated with each molecule of calcium sulfate. In addition to the mined gypsum, synthetic gypsum can be obtained from a byproduct of flue gas desulfurization processes at a power plant. Flue gas that includes sulfur dioxide is wet scrubbed with lime or limestone. Calcium from the lime combines with the sulfur dioxide to form calcium sulfite.

$$CaCO_3 + SO_2 \rightarrow CaSO_3 + CO_2$$

Via forced oxidation, the calcium sulfite is converted to calcium sulfate.

$$CaSO_3 + 2H_2O + \tfrac{1}{2}O_2 \rightarrow CaSO_4 \cdot 2H_2O$$

In manufacturing gypsum products, mined gypsum or synthetic gypsum is calcined in order to remove water and produce calcined gypsum, also known as Plaster of Paris, stucco, calcium sulfate half-hydrate or calcium sulfate hemihydrate. Calcined gypsum, stucco and hemihydrate are the most commonly used terms, and they are used interchangeably in this application. Gypsum products can be obtained by mixing stucco with water and other components of choice to prepare a gypsum slurry which is formed into various products and is allowed to set.

Sulfur may be present in raw or synthetic gypsum as a contaminant. It can be also present in gypsum products such as wallboard. High amounts of sulfur in a gypsum product are implicated in a variety of housing market complaints related to odors, copper pipe and wiring corrosion, and occupant illness. Thus, it is important to test for the amount of sulfur present in gypsum before the gypsum is used for manufacturing of gypsum products.

A standardized ASTM method D-5504 can be used for detecting reduced sulfur in a gypsum product, however this method requires some stationary and elaborate equipment and is mostly suited for detecting reduced sulfur in a gypsum product. Other available test kits include ULS-Diesel Test Kit from Herguth Laboratories. This test is based on a reaction with potassium permanganate. However, a gypsum sample has to be dissolved first in mineral spirits before the gypsum sample can be tested for sulfur with potassium permanganate.

There is a need for a method by which sulfur can be detected in mined or synthetic gypsum right at the mining site or at the recycling plant and prior to using resources and energy for mining, transporting and calcining gypsum.

SUMMARY

A method is provided for rapid detection of sulfur in a gypsum sample, which can be performed in less than an hour and on-site. The method is based on causing emission of sulfur as vapors from a gypsum sample, reacting the vapors with silver nitrate and detecting the sulfur by monitoring for color change.

One embodiment provides a method in which a gypsum sample is heated to cause emission of sulfur as vapors. The vapors are collected and reacted with silver nitrate. The presence of sulfur in the gypsum sample is detected by change in color in the reaction between the silver nitrate and the vapors. Various gypsum samples can be analyzed by the method, including natural gypsum, synthetic gypsum, a gypsum product and stucco. At least in some embodiments, the silver nitrate is deposited on a solid support. Various solid supports are suitable for the method, including chromatography paper, filter paper, synthetic paper and polymeric membrane.

In some embodiments, silver nitrate is deposited on chromatography paper, thereby creating a detection strip which then is secured inside of a carrier lid. The gypsum sample is placed in a heat-resistant container and the carrier lid is assembled with the container. The container is heated and sulfur is detected by change in color on the detection strip. Further embodiments include quantitative colorimetric measurements in which a sulfur detection method with silver nitrate is performed in parallel with gypsum standards for which concentration of sulfur is known.

Other embodiments provide a kit for detecting sulfur in a gypsum sample. The kit includes at least one detection strip and at least one detection device. The detection strip comprises silver nitrate deposited on a solid support and the detection device comprises a heat-resistant container and a carrier lid which can be assembled with the container such that there is substantially no air-leakage from the container when the container is covered with the lid. The kit may further comprise at least one gypsum standard in which the concentration of sulfur is known. The carrier lid can be equipped with at least one means for securing the detection strip inside of the carrier lid.

Further embodiments include methods for detecting sulfur in a mined gypsum sample, in which the mined gypsum sample is placed in a heat-resistant container with an air-tight lid. A piece of chromatography paper saturated with a silver nitrate solution is obtained and secured inside of the air-tight lid. The container is closed with the lid and heated for at least one minute. The piece of chromatography paper is recovered from the lid and the determination is made that the gypsum sample comprises sulfur if the piece of chromatography paper has changed its color after the exposure to the vapors from the gypsum sample.

DETAILED DESCRIPTION

One embodiment provides a method with a silver compound for detecting sulfur in mined or synthetic gypsum. The detection method is based on reacting sulfur emitted from the gypsum sample with a silver compound and obtaining silver sulfide ($Ag_2S$) which can be detected based on its distinct grayish-black metallic color. The method can be performed in field conditions and is appropriate for conducting a test at a mining site and/or at a manufacturing facility before gypsum is calcined and used for making a gypsum product.

In further embodiments, the method can be used for quantifying the amount of sulfur in a gypsum sample. The method is sensitive and accurate for detecting and quantifying sulfur in part-per-million (ppm) amounts in a gypsum sample.

Further embodiments include methods which can be used for detecting and/or quantifying sulfur in gypsum products including such products, but not limited to the same, as wallboard, gypsum panels, joint compounds and the like.

Various silver compounds can be used in the method. The term "silver compound" is understood broadly and includes any and all compounds which comprise silver. Such compounds may include, but are not limited to, silver, silver oxide, silver hydroxide and silver salts. The term "silver salt" is understood broadly and includes organic and inorganic salts of silver. Examples of silver salts include, but are not limited to, silver nitrate, silver bromate, silver carbonate, silver chloride, silver cyanate, silver citrate, silver fluoride, silver iodide, silver lactate, silver nitrite and silver phosphate. In one preferred embodiment, a silver compound is silver nitrate ($AgNO_3$).

One embodiment provides a method for detecting sulfur in a gypsum sample with silver nitrate. The method is easy to complete and can be conducted within a short period of time. In some embodiments, the method can be performed in less than 1 hour. In some embodiments, a solution of silver nitrate is used for detecting sulfur in a gypsum sample. Various solutions of silver nitrate can be used. In some methods, silver nitrate is used in a concentration from 0.10% to 10%. In other methods, silver nitrate is used in a concentration from 0.10% to 5%. In other methods, silver nitrate is used in a concentration from 0.10% to 2%. At least in some methods, silver nitrate is used in a concentration of about 0.25%. Various solvents can be used for preparing a silver nitrate solution, including water.

In some methods, silver nitrate can be dissolved in an alcohol to prepare a stock solution with a predetermined concentration, such as for example, any concentration in the range from 0.10% to 10%. At least in some embodiments, silver nitrate is prepared as a 0.25% solution in alcohol. At least in some methods, alcohol is isopropanol or ethanol. At least in some methods, alcohol is used as a 90% solution. A silver nitrate solution can be prepared by obtaining a 90% solution of isopropanol and weighing and dissolving silver nitrate in the isopropanol solution to obtain a silver nitrate solution with a predetermined concentration. In other embodiments, a water-based stock solution of silver nitrate can be diluted with isopropanol to a working concentration in the range from 0.10% to 10%.

In some embodiments, a sulfur detection method is completed by pre-heating a gypsum sample to cause emission of sulfur as vapors and then reacting the vapors with silver nitrate. The reaction between silver nitrate which is colorless and the vapors produces silver sulfide which can be detected because of its distinct color.

While some embodiments are performed with a silver nitrate solution, other embodiments can be conducted with any silver compound which can be reacted with vapors from a pre-heated gypsum sample.

While some methods can be performed with a silver compound in solution, other embodiments are conducted with a silver compound deposited on a solid support. Various solid supports can be used without limitation, including, but not limited to, natural paper, synthetic paper, polymeric membrane and the like. In some embodiments, filter paper can be used. In further embodiments, chromatography paper can be used. Suitable paper includes filter and chromatography paper sold under the brand name WHATMAN™ available from Sigma-Aldrich, Inc.

Figure 1:
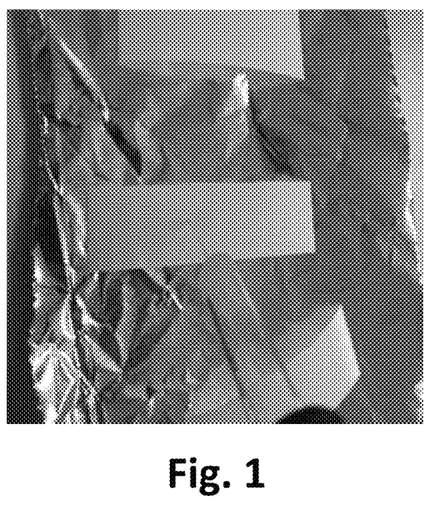
FIG. 1 depicts preparation of a detection strip.
Figure 2:
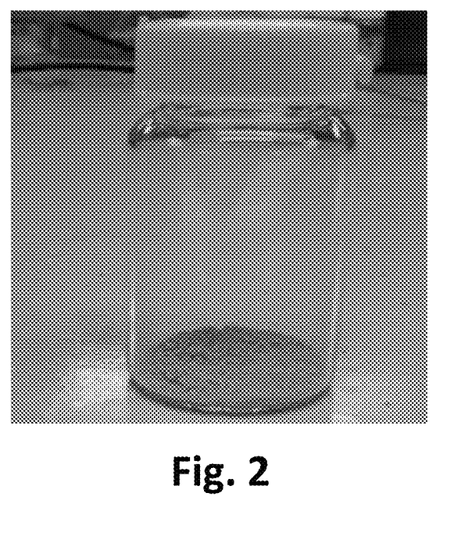
FIG. 2 depicts a container with a gypsum sample to be tested.

In further embodiments, a detection strip is obtained by depositing a drop of a silver nitrate solution on a piece of chromatography paper and allowing the drop to dry, as shown in FIG. 1. A gypsum sample is weighed and placed in a heat-resistant container, as shown in FIG. 2. Suitable containers include heat-resistant vials, beakers, flasks, bottles and test tubes. A heat-resistant container can be made from heat-resistant glass, ceramic, metal or metal alloy.

Figure 3:
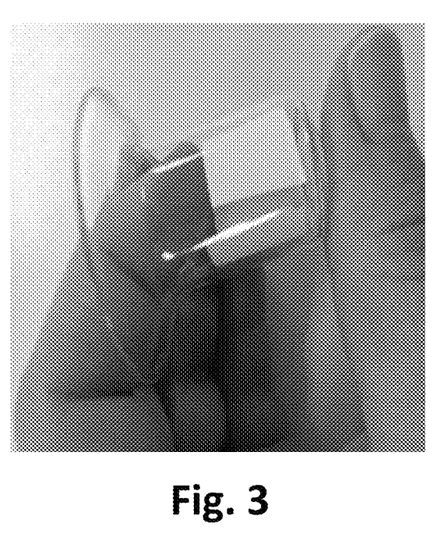
FIG. 3 depicts placement of a detection strip into a carrier lid.

The detection strip is deposited inside of a carrier lid. The carrier lid can be made from heat-resistant glass or any other heat-resistant material. The carrier lid can be in a bell-like shape as shown in FIG. 3 and designed such that it holds the detection strip in place as shown in FIG. 3, and prevents it from slipping out from the lid after the lid is placed over the container with the gypsum sample, as shown in FIG. 4.

In further embodiments, the carrier lid can be equipped with at least one set of means selected from the following: pins, clips, rings, semi-rings, an insert or a gasket for securing the detection strip inside of the carrier lid. The carrier lid can be designed with a slot inside the lid, such that the detection strip is secured in the slot. In further embodiments, a chemical adhesive including, but not limited to, glue can be used for attaching the detection strip inside of the carrier lid.

Figure 4:
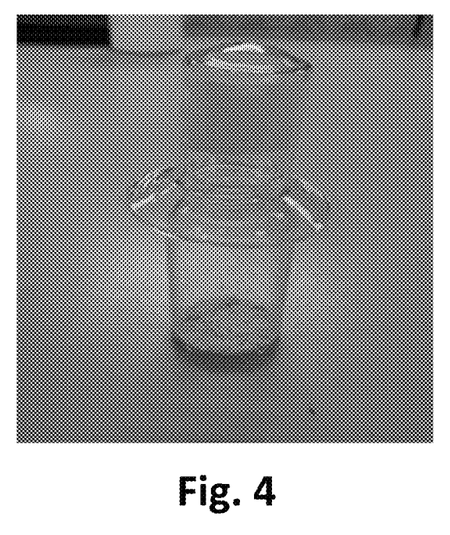
FIG. 4 depicts a detection device comprising a container with a gypsum sample and a carrier lid with a detection strip, fitted on the container.

After the detection strip is secured inside of the carrier lid, the carrier lid is tightly connected to the container with a gypsum sample, as shown in FIG. 4. It is important that the carrier lid with the detection strip is assembled to the container air-tightly such that there is substantially no leak of air or gas vapors from the container because the sulfur detection device is heated to cause emission of vapors from a gypsum sample and it is important to prevent the leakage of vapors from the container.

Figure 5:
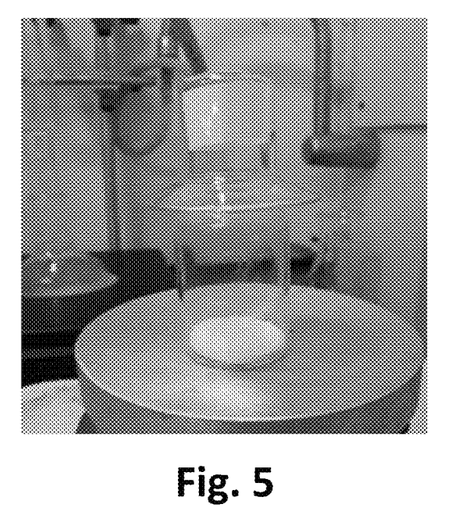
FIG. 5 depicts a process of heating a gypsum sample in a sulfur-detection device and causing emission of vapors.

The sulfur detection device which comprises a container with the attached carrier lid can be heated on a hot plate, as shown in FIG. 5. In other embodiments, the sulfur detection device can be heated by any other means suitable for heating a heat-resistant container. Such means include, but are not limited to, a gas burner, a conventional oven and a microwave oven.

At least in some embodiments, the heating can be carried out at a controlled temperature. The heating can be carried out for a predetermined period of time. In some embodiment, a gypsum sample is heated for at least 1 minute, at least 2 minutes, at least 3 minutes, at least 4 minutes, at least 5 minutes, at least 6 minutes, at least 7 minutes, at least 8 minutes, at least 9 minutes, at least 10 minutes. In further embodiments, a gypsum sample is heated for a period of time from 1 minute to 30 minutes. In further embodiments, a gypsum sample is heated for a period of time from 1 minute to 10 minutes. In further embodiments, a gypsum sample is heated for a period of time from 1 minute to 5 minutes.

Further embodiments provide a kit for detecting sulfur in a gypsum sample. The kit comprises at least one detection strip and a sulfur detection device. The detection strip comprises at least one silver compound deposited on a solid support. The silver compound can be silver nitrate. The solid support can be chromatography paper. The detection device comprises a carrier lid and a container such that the carrier lid can cover the container air-tightly with substantially no vapor leakage from the container to the outside environment when the carrier lid is assembled with the container. The kit can further comprise at least one gypsum standard sample with a known concentration of sulfur.

Figure 6:
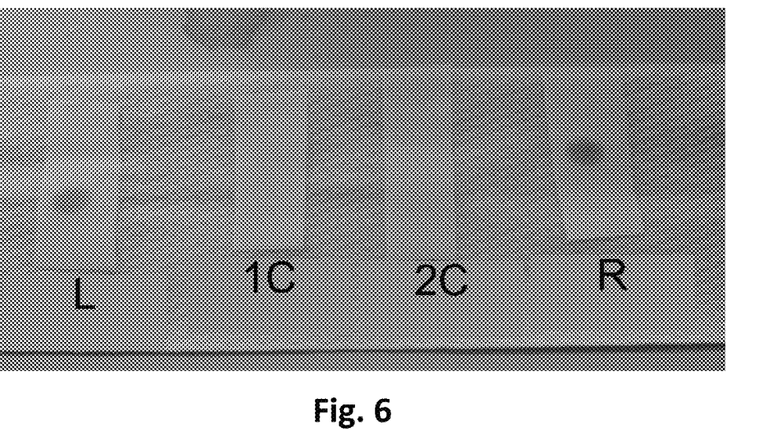
FIG. 6 shows results of a sulfur detection test with silver nitrate: the right and the left detection strips are positive for sulfur and the two center strips are negative.

After the reaction with the detection strip is completed in the detection device, the detection strip is removed from the carrier lid and examined. FIG. 6 shows four detection strips from tests with four different gypsum samples. The right (R) and left (L) samples are positive for sulfur as evidenced by colored circles on the test strips, while the two center strips (1C and 2C) remain colorless, suggesting that these gypsum samples do not contain sulfur above the detection limit. The intensity of the color on the detection strip is dependent on the amount of sulfur originally present in a gypsum sample. The higher is the concentration of sulfur, the darker is the color of the circle on the detection strip.

In further embodiments, a sulfur detection method can be modified to quantitate the amount of sulfur in a gypsum sample. In such embodiments, standards are provided which comprise gypsum samples with known concentrations of sulfur. At least one such standard with a known sulfur concentration can be tested along with a gypsum sample for which a concentration of sulfur is to be determined. After the reaction is completed, the color intensity of the standard is compared to that of a gypsum sample. In further embodiments, several standards with gradually increasing known concentrations of sulfur can be used for accurate quantification of the amount of sulfur in a gypsum test sample. Some sulfur detection methods include those in which sulfur can be detected in a ppm amount. At least some methods have a sulfur detection threshold of 1 ppm.

It will be appreciated that these sulfur detection methods can be conducted with mined raw gypsum, synthetic gypsum, gypsum products or stucco. As shown in Table 1 below, various gypsum samples, gypsum board samples, stucco samples and gypsum samples from various quarries were tested for sulfur with silver nitrate as described above. The results of the tests are reported in the right column under the QC method in Table 1. The samples were also tested by a conventional spectroscopic method as shown in the left column under the Columbia Lab Result in Table 1.

TABLE 1

| Sample ID | Sulfur Concentration (ppm) (Columbia Lab Result) | Sulfur Presence (Yes/No), QC Method |
|---|---|---|
| Landplaster | | |
| Gypsum 01 | 67 | Y |
| Gypsum 02 | 67 | Y |
| Gypsum 04 | 58 | Y |
| Gypsum 05 | 53 | Y |
| Gypsum 06 | 86 | Y |
| Gypsum 11 | 53 | Y |
| Gypsum 12 | 55 | Y |
| Gypsum 13 | 59 | Y |
| Gypsum 14 | 52 | Y |
| Gypsum 15 | 70 | Y |
| Board | | |
| Board 01 | 7.9 | Y |
| Board 02 | 7.0 | Y |
| Board 04 | 7.2 | Y |
| Board 05 | 7.9 | Y |
| Board 06 | 7.7 | Y |
| Board 11 | 9.0 | Y |
| Board 12 | 7.4 | Y |
| Board 13 | 7.5 | Y |
| Board 14 | 7.8 | Y |
| Board 15 | 9.6 | Y |
| Quarry | | |
| Gypsum 1 | 29 | Y |
| Gypsum 2 | 13 | Y |
| Gypsum 3 | 690 | Y |
| Gypsum 4 | 100 | Y |
| Gypsum 5 | 460 | Y |
| Gypsum 6 | 11 | Y |
| Gypsum 7 | 120 | Y |

As can be seen from Table 1, a sulfur detection method with silver nitrate accurately detects the presence of sulfur in these samples. This includes gypsum samples in which the concentration of sulfur is less than 10 ppm, but more than 1 ppm.

One of the advantages of the sulfur detection method with silver nitrate is that it is easy to set up and it can be completed in less than one hour. Further, the results are reproducible. As shown in Table 2 below, several samples were tested by two technicians independently. Both technicians, tester R and tester N, obtained similar results. Further, the test results obtained by a sulfur detection method with silver nitrate correlate with detection of sulfur by a spectroscopic method in a laboratory.

TABLE 2

| Sample ID | Sample Type (Land Plaster (LP) or stucco) | Sulfur Presence (Yes/No), QC Method, tester R | Sulfur Presence (Yes/No), QC Method, tester N | Sulfur Concentration in ppm (Columbia Lab Result) |
|---|---|---|---|---|
| Gypsum 3 Quarry | LP | Y | Y | 690 |
| Gypsum 4 | LP | Y | Y | 100 |
| Gypsum 6 Quarry | LP | Y | Y | 11 |
| Land Plaster | LP | N | N | |
| Gypsum Synthetic stucco | LP Stucco | N N | N N | |

Figure 7:
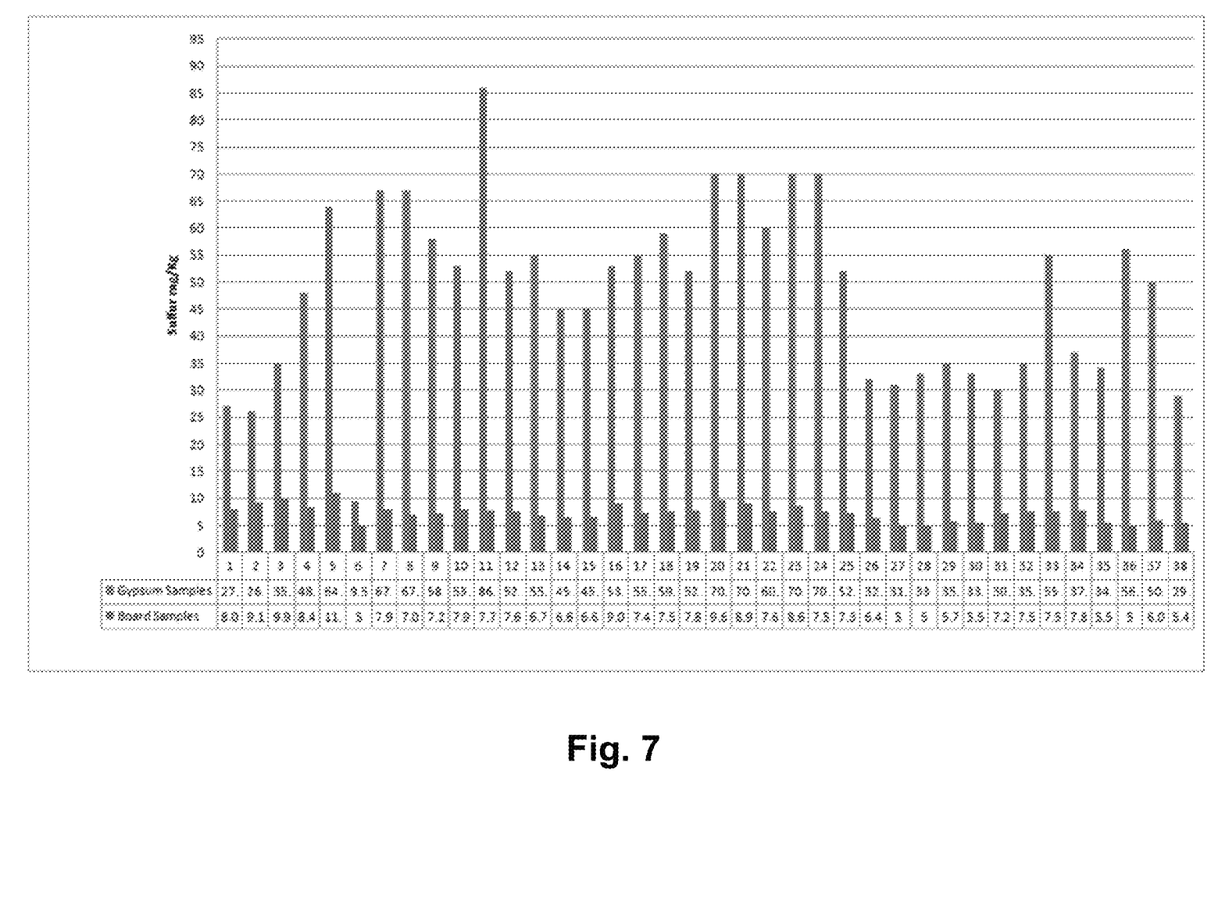
FIG. 7 reports a comparative analysis for amount of sulfur detected in gypsum samples (the left bar in each pair) versus corresponding gypsum boards prepared from the gypsum samples (the right bar in each pair)
Figure 8:
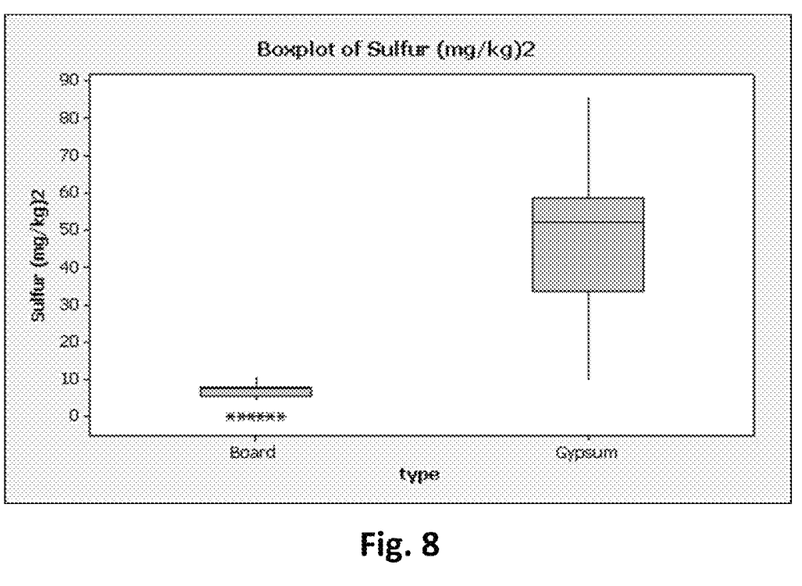
FIG. 8 is a comparative plot showing the amount of sulfur in gypsum and in gypsum board made from the gypsum.

Further advantages of a sulfur detection method with silver nitrate include savings in energy and labor. As described above, the method can be used for detecting sulfur in freshly mined gypsum right at the mining site. FIG. 7 reports a correlation between the amount of sulfur present in gypsum and the amount of sulfur present in a gypsum product prepared with the gypsum. This point is further illustrated by boxplot data in FIG. 8 in which the amount of sulfur in gypsum and corresponding gypsum board is plotted in $mg/kg^2$.

As shown in FIG. 7, if gypsum contains a high amount of sulfur (the left bar for each of the 38 samples), a gypsum product prepared from the gypsum (the right bar for each of the 38 samples) will contain the amount of sulfur higher than a gypsum product prepared from gypsum with lesser amount of sulfur. Thus, if gypsum is tested for sulfur by a sulfur detection method with silver nitrate and high amounts of sulfur are detected, the gypsum is not calcined and is not used for manufacturing of a gypsum product which would not suitable for its intended purpose because of toxically high levels of sulfur. Cost savings and energy savings are achieved by utilizing a sulfur detection method with silver nitrate when gypsum is tested prior to being taken into a manufacturing process.

The invention will be further explained by the way of the following non-limiting examples.

Example 1

A 0.25% solution of silver nitrate in 90% alcohol solution was prepared. A drop of the solution was deposited on a strip of chromatography paper and was allowed to dry, as shown in FIG. 1.

The paper was put in a glass top hat which is a bell-like lid shown in FIG. 3. A sample of gypsum to be tested was weighed and mixed 1:4 with a sample of analytical grade gypsum. The combined gypsum sample in the amount of 0.5 g was placed in a glass vial, as shown in FIG. 2. The top hat was fitted over the vial, as shown in FIG. 4. The combined test specimen and reactant were heated rapidly using a micro-hot plate, as shown in FIG. 5. After 3 minutes, the sample was removed from the heat and the chromatography paper strips were examined. Specimens that developed a brownish spot, comprise at least 10 PPM or more sulfur, as shown in FIG. 6, the right and the left samples. Samples that did not develop color comprise less than 10 PPM of sulfur, as shown in FIG. 6, the 2 center samples.

Example 2

Figure 9:
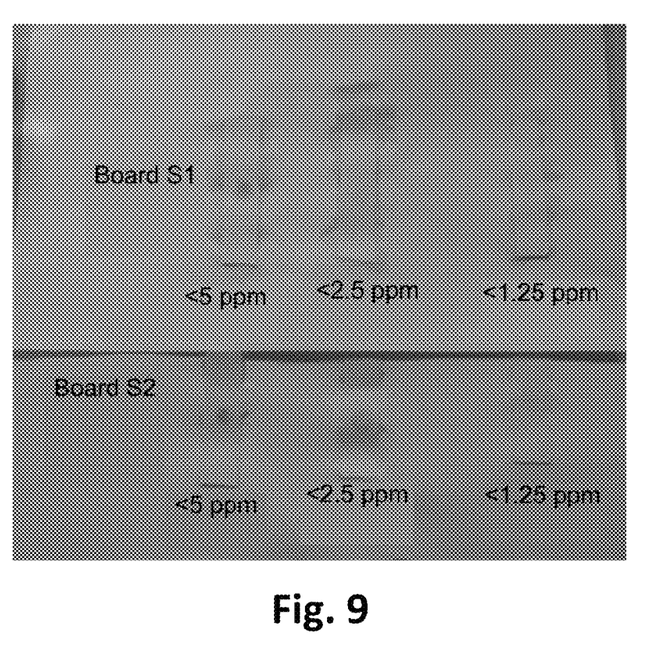
FIG. 9 depicts results of testing detection limits for the sulfur detection method with silver nitrate.

The detection limit for a sulfur detection method with silver nitrate was determined by a series of gypsum sample dilutions. In this experiments, 0.5 of a gypsum sample was tested as is or mixed in 50:50 and 25:75 ratios with gypsum for which sulfur concentration was known. All samples were then subjected to a sulfur detection method with silver nitrate as provided in Example 1. The results of these tests are shown in FIG. 9 in which sulfur was detected in the sample analyzed and in its 50:50 dilution, but not in the 25:75 dilution of the sample.

Further tests were conducted with gypsum board samples and these results are listed in Table 3 below. As shown in column "QC Method," the sulfur detection method with silver nitrate detects sulfur in board samples with concentration of sulfur at 2 ppm and more. At the same time, a spectroscopic lab test detects sulfur in samples with concentration of sulfur at 5 ppm and more, as shown in column "Columbia Lab Result."

TABLE 3

| Sample ID Board | Sulfur Concentration (ppm) (Columbia Lab Result) | Sulfur Presence (ppm) (Yes/No), QC Method |
| --- | --- | --- |
| Board 03 | <5 | <2 |
| Board 21 | <5 | <2 |
| Board 22 | <5 | <2 |
| Board 29 | <5 | <2 |

What is claimed is:

1. A method for detecting sulfur in a gypsum sample, the method comprising:
   heating the gypsum sample and causing emission of sulfur in vapors;
   collecting the vapors;
   reacting the vapors with silver nitrate; and
   detecting the presence of sulfur in the gypsum sample by change in color in the reaction between the silver nitrate and the vapors;
   wherein the gypsum sample is selected from the group consisting of: gypsum, synthetic gypsum, gypsum product and stucco; and
   wherein the silver nitrate is deposited on a solid support.

2. The method of claim 1, wherein the vapors are reacted with the silver nitrate deposited on chromatography paper.

3. The method of claim 1, wherein the gypsum sample is heated in a heat-resistant container.

4. The method of claim 1, wherein the silver nitrate is deposited on chromatography paper, thereby creating a detection strip;
   the detection strip is secured inside of a carrier lid;
   the gypsum sample is placed in a container; and
   the carrier lid is assembled with the container prior to the step of heating the gypsum sample.

5. The method of claim 1, wherein the method is performed in parallel with at least one gypsum standard in which a concentration of sulfur is known and wherein a concentration of sulfur in the gypsum sample is determined by comparing the intensity of color change in the reaction with the gypsum sample to the intensity of color change in the reaction with the gypsum standard.

6. A method of claim 1, wherein the silver nitrate is a silver nitrate solution with concentration from 0.1% to 10%.

7. The method of claim 2, wherein the silver nitrate is deposited on chromatography paper by exposing the chromatography paper to a silver nitrate solution and then allowing the chromatography paper to dry before it is reacted with the vapors.

8. The method of claim 7, wherein the silver nitrate solution is 0.25% of silver nitrate in 90% isopropanol.

9. The method of claim 1 wherein a threshold of the method is 10 ppm of sulfur.

10. The method of claim 3, wherein the heat-resistant container is a glass vial and the lid has a bell-like shape.

11. The method of claim 1, wherein the method is performed in field conditions.

* * * * *